United States Patent
Stenzler et al.

(10) Patent No.: US 9,968,125 B2
(45) Date of Patent: *May 15, 2018

(54) NICOTINE—DIKETOPIPERAZINE MICROPARTICLE FORMULATIONS AND METHODS OF MAKING THE SAME

(71) Applicant: Philip Morris Products S.A., Neuchatel (CH)

(72) Inventors: Alex Stenzler, Long Beach, CA (US); Noe Zamel, Ontario (CA); Arthur Slutsky, Ontario (CA); Steven Ellis, Ontario (CA)

(73) Assignee: Philip Morris Products S.A. (CH)

( * ) Notice: Subject to any disclaimer, the term of this patent is extended or adjusted under 35 U.S.C. 154(b) by 366 days.

This patent is subject to a terminal disclaimer.

(21) Appl. No.: 14/593,633

(22) Filed: Jan. 9, 2015

(65) Prior Publication Data

US 2016/0198758 A1   Jul. 14, 2016

(51) Int. Cl.
| | |
|---|---|
| *A61K 9/14* | (2006.01) |
| *A61K 9/16* | (2006.01) |
| *A61K 31/44* | (2006.01) |
| *A24B 15/16* | (2006.01) |
| *A24F 47/00* | (2006.01) |
| *A61K 31/465* | (2006.01) |
| *A61K 31/495* | (2006.01) |
| *A61K 9/50* | (2006.01) |

(52) U.S. Cl.
CPC ............ *A24B 15/16* (2013.01); *A24F 47/002* (2013.01); *A61K 31/465* (2013.01); *A61K 9/1694* (2013.01); *A61K 9/5084* (2013.01); *A61K 31/495* (2013.01)

(58) Field of Classification Search
CPC .. A61K 9/0075; A61K 31/465; A61K 31/495; A61K 9/1694; A61K 9/5084
USPC .................. 514/356; 424/489, 490
See application file for complete search history.

(56) References Cited

U.S. PATENT DOCUMENTS

| | | | |
|---|---|---|---|
| 5,746,227 A | 5/1998 | Rose et al. | |
| 6,234,169 B1 | 5/2001 | Bulbrook et al. | |
| 6,799,576 B2 | 10/2004 | Farr | |
| 8,182,838 B2 | 5/2012 | Morton et al. | |
| 8,227,409 B2 | 7/2012 | Kraft et al. | |
| 8,256,433 B2 | 9/2012 | Gonda | |
| 8,381,739 B2 | 2/2013 | Gonda | |
| 8,440,231 B2 | 5/2013 | Smyth et al. | |
| 8,668,934 B2 | 3/2014 | Vehring et al. | |
| 8,689,803 B2 | 4/2014 | Gonda | |
| 8,741,348 B2 | 6/2014 | Hansson et al. | |
| 9,585,835 B1 * | 3/2017 | Stenzler ............... | A61K 9/0075 |
| 2003/0103908 A1 | 6/2003 | Piskorz | |
| 2007/0292519 A1 | 12/2007 | Piskorz | |
| 2008/0020048 A1 | 1/2008 | Snape et al. | |
| 2010/0317574 A1 | 12/2010 | Kraft et al. | |
| 2011/0082076 A1 | 4/2011 | Dellamary et al. | |
| 2011/0268809 A1 | 11/2011 | Brinkley et al. | |
| 2012/0042886 A1 | 2/2012 | Piskorz | |
| 2012/0138056 A1 | 6/2012 | Morton et al. | |
| 2013/0098377 A1 | 4/2013 | Borschke et al. | |
| 2013/0209540 A1 | 8/2013 | Duggins et al. | |
| 2013/0323179 A1 | 12/2013 | Popov et al. | |
| 2014/0166027 A1 | 6/2014 | Fuisz et al. | |
| 2014/0212504 A1 | 7/2014 | Weers et al. | |
| 2014/0234392 A1 | 8/2014 | Hansson et al. | |
| 2014/0261474 A1 | 9/2014 | Gonda | |
| 2015/0031609 A1 | 1/2015 | Steiner et al. | |

FOREIGN PATENT DOCUMENTS

| | | |
|---|---|---|
| CA | 2146954 | 10/1996 |
| CA | 2265198 | 9/1999 |
| WO | 2005/107872 | 11/2005 |
| WO | 2014/066856 | 5/2014 |
| WO | 2015/166344 | 11/2015 |
| WO | 2015/166350 | 11/2015 |

OTHER PUBLICATIONS

Benowitz et al., 2009, "Nicotine Chemistry, Metabolism, Kinetics and Biomarkers. Hanb. Ex. Pharmacol.," (192): 29-60.

* cited by examiner

*Primary Examiner* — Kevin E Weddington
(74) *Attorney, Agent, or Firm* — Mueting, Raasch & Gebhardt, P.A.

(57) ABSTRACT

This invention relates to nicotine microparticles formulations made with the help of a diketopiperazine compound, in particular fumaryl diketopiperazine (FDKP). The invention relates to the various types of microparticles that can be made, in particular nicotine-coated and nicotine-loaded microparticles. The invention further relates to the various methods that can be used in making the microparticles. One particular method involves making FDKP microparticles which are further surface-coated with nicotine. Another particular method involves mixing nicotine with $FDKP^{2-}$ and/or FDKP and then forming microparticles which contain nicotine throughout their volume. The invention also relates to the use of this microparticles in tobacco related therapies, such as tobacco replacement or tobacco withdrawal.

9 Claims, 6 Drawing Sheets

Figure 1:
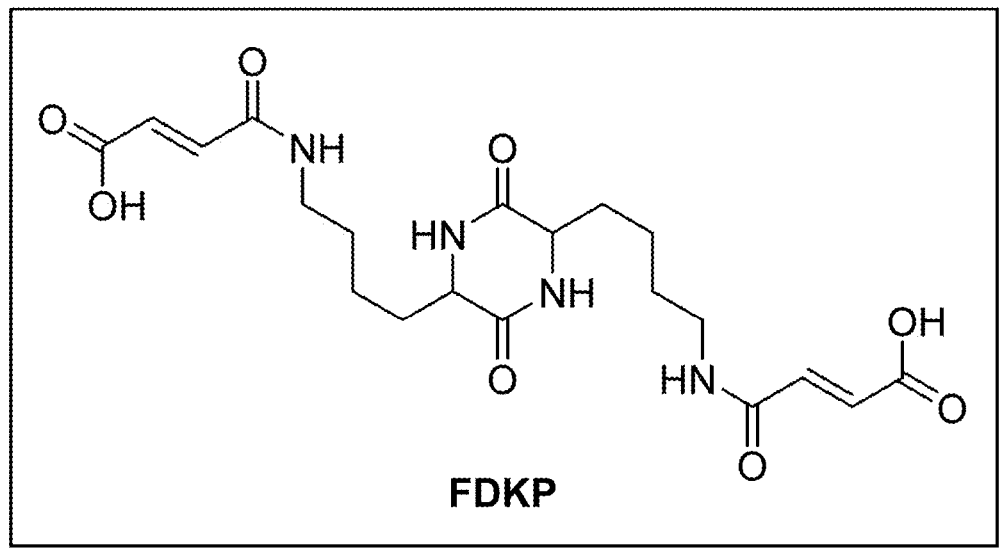
Figure 2:
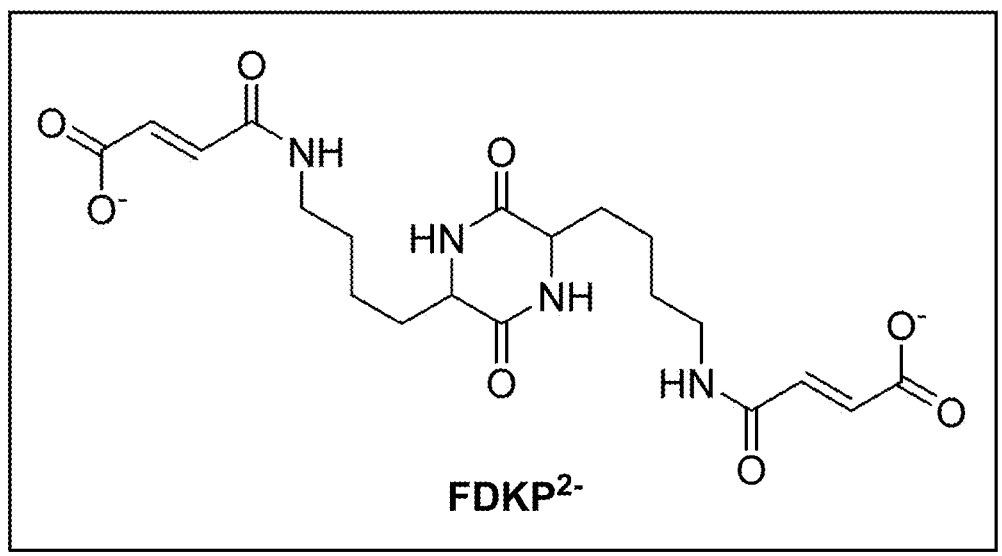
Figure 3:
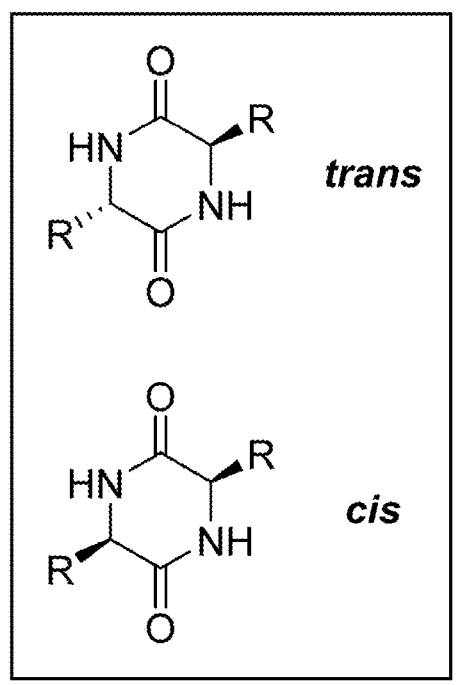
Figure 4:
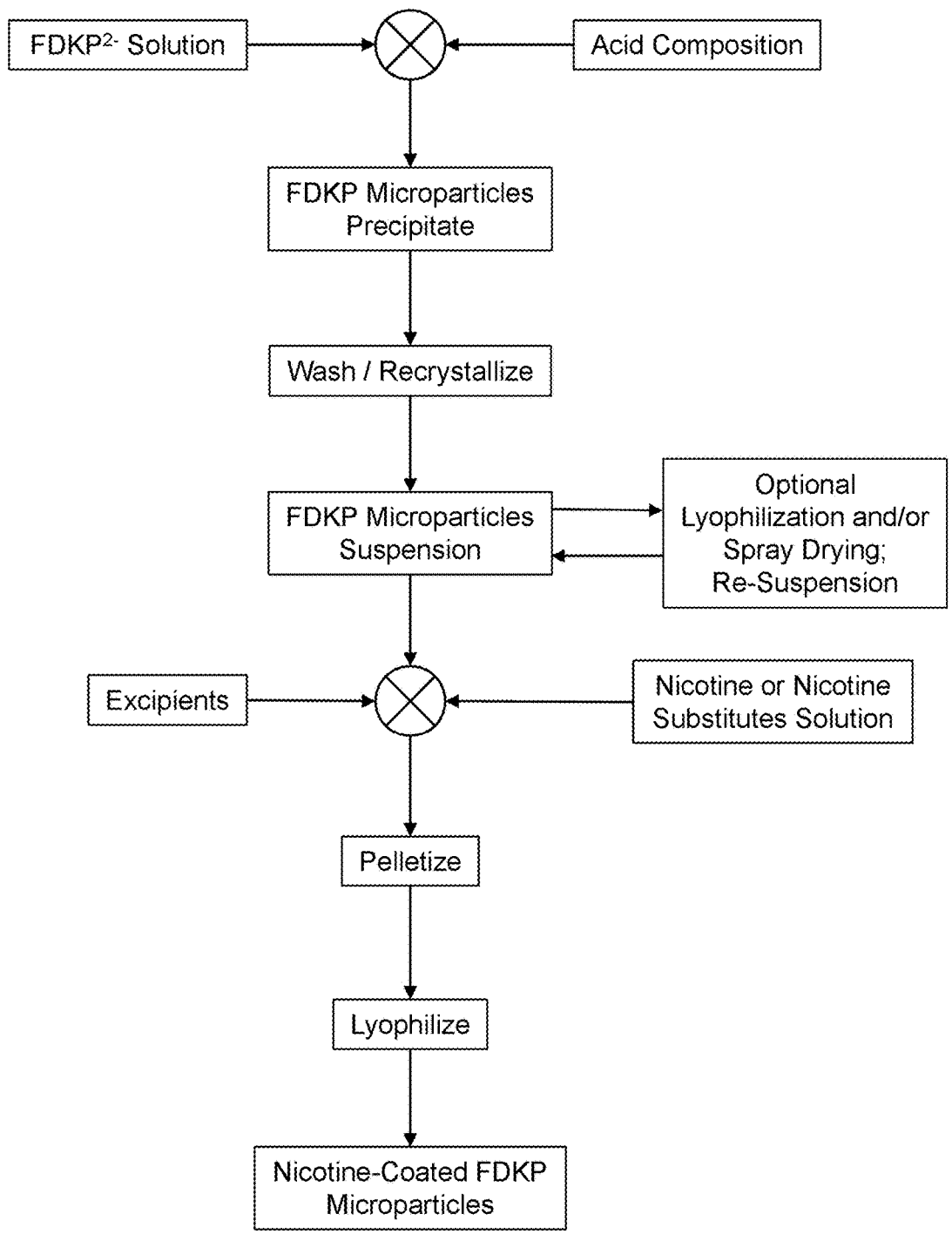

```
            ┌─────────────┐
            │ Excipients  │
            └──────┬──────┘
                   │
                   ▼
┌──────────────────┐      ┌──────────────────────┐
│ FDKP and/or FDKP²⁻│─────▶⊗◀─────│ Nicotine or Nicotine │
│    Solution      │      │ Substitute Solution  │
└──────────────────┘      └──────────────────────┘
                   │
                   ▼
            ┌─────────────┐
            │  Spray Dry  │
            └──────┬──────┘
                   │
                   ▼
        ┌──────────────────────────┐
        │  Nicotine-Loaded FDKP    │
        │ and/or FDKP²⁻ Microparticles │
        └──────────────────────────┘
```

Figure 5

Fig. 6A

Nicotine-coated
FDKP microparticle

Fig. 6B

Nicotine-loaded
FDKP and/or FDKP$^{2-}$
microparticle

Figure 6

NICOTINE—DIKETOPIPERAZINE MICROPARTICLE FORMULATIONS AND METHODS OF MAKING THE SAME

BACKGROUND OF THE INVENTION

Smoking has been determined to be a contributory or causative factor in a number of diseases including respiratory diseases such as emphysema, chronic bronchitis, lung infections and lung cancer. Most regular smokers become addicted to, or dependent upon, the pharmacological effects of nicotine in tobacco smoke. A common strategy in overcoming a nicotine addiction is the administration of daily doses of nicotine which are therefrom gradually reduced until complete elimination.

It is believed that cigarette smoke contains approximately 4000 chemical compounds and has a range of particle sizes from less than 0.1 micron to approximately 0.5 micron. During inhalation, it is known that most particles larger than 10-12 micron in size typically can't make the turn in the oral cavity to enter the lower respiratory tract and instead impact the back of the throat. While particles less than 5 micron in size are generally considered respirable and can thus enter the lower respiratory tract, the majority of particles less than 1 micron in size do not settle in the alveoli, and are thus expelled during subsequent exhalation.

The state of the art in the development of nicotine inhalation products designed to replace traditional cigarettes, is to replicate or match the particles found in cigarettes. For example, such replacement technologies include e-cigarettes that produce nicotine vapor, ultrasonically produced nicotine aerosol droplets or nicotine oral sprays. These replacement cigarette technologies typically produce particles that are less than 0.5 micron in size, and very large particles that are greater than 10-12 micron in size. However, each of these technologies suffer from the same result—in that less than half of the inhaled nicotine and associated compounds remain in the lungs and the balance is exhaled into the environment. Unfortunately, this means that the public must still contend with the same problem of users of these technologies producing what is effectively second hand smoke, and accordingly these technologies are increasingly being banned in selected public spaces.

Self-propelled aerosols (also known as pressurized aerosols) which contain nicotine in solution have also been proposed as cigarette substitutes. An example is the self-propelled formulation of Jacobs (U.S. Pat. No. 4,635,651). As shown in Jacobs, these delivery systems contain a water-based aerosol formulation and a propellant such as freon, which are stored in a pressurized container. When actuated, Jacobs delivers nicotine and a solid carrier to the mouth of the user. Thus the aerosol created by Jacobs contains, in combination, a mixture of nicotine and the solid carrier. The nicotine is not formed as a composite part of the solid carrier. Further, the particle size of the aerosol created by Jacobs was variable. Therefore, the dose which is administered by using such pressurized aerosols may not be accurately controlled. It has also been proposed to produce a dry powder inhaler for delivering a nicotine containing medicament via inhalation (see PCT application PCT/CA95/00562).

While nicotine formulations in the form of salts and complexes have been developed, there is still a need for nicotine formulations adapted for inhalation into the alveoli and smaller airways of the lungs, while reducing or eliminating exhalable nicotine by a subject. The present invention satisfies this need.

SUMMARY OF THE INVENTION

According to the instant invention, a nicotine formulation, which more closely simulates cigarette smoke, is provided which may be used with existing inhaler technology so as to improve the effectiveness of tobacco replacement or withdrawal therapies.

In accordance with the method of the instant invention, there are provided composite materials comprising discrete particles which are a mixture of nicotine and one or more carriers. As with cigarette smoke, the composite materials are physical combinations of both the nicotine and the carriers. The carriers effectively provide particles having a size range and density such that it will be conveyed on inhalation to the alveoli and lower airways of a person. The nicotine is combined with the carriers such that it will be conveyed to the alveoli and lower airways of a person with the carriers. In accordance with the instant invention, the nicotine and carriers are physically combined in such ways that the resulting composite materials will not separate during inhalation.

The present invention relates to dry powder nicotine formulations suitable for inhalation. The formulations include particles that are substantially between about 1-10 micron in size. In one embodiment, the particles are substantially between about 2-5 micron in size. In another embodiment, less than about 10% of the nicotine particles are less than about 1 micron in size. In another embodiment, less than about 10% of the particles are less than about 2 micron in size. In another embodiment, at least about 90% of the particles are less than about 10 micron in size. In another embodiment, at least about 90% of the particles are less than about 5 micron in size. In another embodiment, less than about 10% of the particles are less than about 1 micron in size and wherein at least about 90% of the particles are less than about 10 micron in size. In another embodiment, less than about 10% of the particles are less than about 2 micron in size and wherein at least about 90% of the particles are less than about 5 micron in size.

The present invention relates to dry powder nicotine-coated FDKP microparticles, and nicotine-loaded FDKP and/or $FDKP^{2-}$ microparticles. In the preferred embodiments of the invention FDKP is used as a carrier, where F stands for the fumaryl substituent. In other embodiments it can be replaced by succinyl, maleyl, and glutaryl.

The present invention relates to dry powder nicotine-coated FDKP microparticles suitable for inhalation, and methods of making thereof. In one embodiment the invention relates to microparticles comprising an FDKP core coated with a nicotine or nicotine substitute formulation, herein referred to as "nicotine-coated microparticles." In another embodiment the invention relates to methods of making nicotine-coated formulated microparticles comprising the following steps:

a) adding an acidic composition to an $FDKP^{2-}$ salt solution;

b) precipitating the FDKP microparticles into a suspension, followed by optional recrystallization;

c) mixing this suspension with a liquid nicotine or nicotine substitute formulation;

d) pelletization and lyophilization of the solution.

The nicotine or nicotine substitute formulation will be solubilized in a liquid carrier. In one embodiment, the liquid carrier may comprise water and preferably consists of water. In another embodiment, the liquid carrier additionally comprises alcohol, particularly where the nicotine is a nicotine salt such as a nicotine sulphate or a nicotine tartrate. In this case, alcohol may be added as a cosolvent, to expedite the solubilization of nicotine or nicotine salt in the flowable mixture. In such a case, the liquid carrier preferably comprises a minor proportion of alcohol and a major proportion of water. The ratio of alcohol to water in the liquid carrier may be from about 1:1 to 1:10, preferably from about 1:2 to 1:8 and more preferably from about 1:5 to 1:7 parts by weight.

The present invention also relates to dry powder homogeneously mixed nicotine and FDKP and/or $FDKP^{2-}$ formulations suitable for inhalation, herein referred to as "nicotine-loaded microparticles," and methods of making thereof. In one embodiment the invention relates to homogeneous microparticles comprising FDKP and/or $FDKP^{2-}$ and nicotine or nicotine substitutes. In another embodiment the invention relates to methods of making the formulated microparticles comprising the following steps:

a) preparing a flowable mixture comprising FDKP and/or $FDKP^{2-}$, nicotine or nicotine substitutes and a liquid carrier;

b) spray drying the flowable mixture to produce dry powder particles comprising FDKP and/or FDKP2–and nicotine, that are substantially between about 1 micron in size and about 10 micron in size, and are suitable for delivery to the alveoli and lower airways of a person.

In one embodiment, the liquid carrier may comprise water and preferably consists of water. In another embodiment, the liquid carrier additionally comprises alcohol, particularly where the nicotine is a nicotine salt such as a nicotine sulphate or a nicotine tartrate. In this case, alcohol may be added as a cosolvent, to expedite the solubilization of nicotine or nicotine salt in the flowable mixture. In such a case, the liquid carrier preferably comprises a minor proportion of alcohol and a major proportion of water. The ratio of alcohol to water in the liquid carrier may be from about 1:1 to 1:10, preferably from about 1:2 to 1:8 and more preferably from about 1:5 to 1:7 parts by weight.

The present invention also relates to a dry powder nicotine formulation suitable for inhalation that includes nicotine based microparticles substantially between about 1-10 micron in size, and cough suppressant having particles substantially between about 5-10 micron in size. In one embodiment, the cough suppressant particles comprises menthol. In another embodiment, the nicotine microparticles are substantially between about 2-5 micron in size and the cough suppressant particles are substantially between about 5-8 micron in size. In another embodiment, the formulation further includes cough suppressant particles substantially between about 10-200 micron in size. In another embodiment, the cough suppressant particles are substantially between about 10-200 micron in size comprises menthol. In another embodiment, the formulation further includes particles comprising a flavor which are substantially between about 10-1000 micron in size. In another embodiment, the flavor particles comprise menthol.

The present invention also relates to methods for conducting tobacco replacement or tobacco withdrawal therapy comprising:

a) preparing nicotine-coated or nicotine-loaded FDKP based microparticles which are suitable for delivery to the alveoli and lower airways of a person and which simulate cigarette smoke when aerosolized and inhaled, and b) packaging the microparticles in containers for use with an inhaler suitable for delivering a medicament to the lungs. The inhaler is preferably non-pressurized. Such inhalers, which may be referred to as breath activated inhalers, utilize the inhalation of a person to produce the air flow through the inhaler.

The present invention relates to nicotine-coated or nicotine-loaded microparticles manufactured in such conditions as to comprise substantially spherical particles. In one embodiment the microparticles are substantially spherical. The spherical shape of the dried particles reduces aggregation of the particles while in the inhaler, thus rendering it easier to aerosolize the particles upon inhalation by the user. In another embodiment the microparticles have a dimpled surface. By having a dimpled surface, the aerodynamics of the microparticles are improved whereby the microparticles may by more easily entrained in the air inhaled by the user.

An advantage of the instant invention is that the medicament particles produced by the method disclosed herein are well adapted for absorption into the bloodstream of a person via the alveoli and small airways of the lungs. The microparticles are composite structures. In the embodiments comprising nicotine-coated microparticles, the composite consist of a FDKP microparticle core with an uninterrupted coating comprising nicotine. In the embodiments consisting of nicotine-loaded microparticles, the composite consist of a homogeneous microparticle comprising FDKP and/or $FDKP^{2-}$, and nicotine. Accordingly, the nicotine will not separate during inhalation from either the nicotine-coated FDKP microparticles or the nicotine-loaded FDKP and/or $FDKP^{2-}$ microparticles. Thus the microparticles of the present invention will convey the nicotine to the lungs in a manner which mimics cigarette smoke. By controlling the conditions at which the microparticles are manufactured, particles having a size from about 0.1 to about 5 μm, more preferably from about 0.5 to about 3 μm may be produced.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1 depicts the chemical structure of FDKP.

FIG. 2 depicts the chemical structure of $FDKP^{2-}$.

FIG. 3 depicts the stereochemical difference between the cis and trans stereoisomers of both FDKP and $FDKP^{2-}$.

FIG. 4 is a flowchart depicting an exemplary method of manufacturing nicotine-coated FDKP microparticles.

FIG. 5 is a flowchart depicting an exemplary method of manufacturing nicotine-loaded FDKP and/or $FDKP^{2-}$ microparticles.

FIG. 6, comprising FIGS. 6A and 6B, is a schematic depiction of a nicotine-coated FDKP microparticle (A), and a nicotine-loaded FDKP and/or $FDKP^{2-}$ microparticle (B).

DETAILED DESCRIPTION

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "dry powder" refers to a fine particulate composition that is not suspended or dissolved in a propellant, carrier, or other liquid, and it is not meant to necessarily imply a complete absence of all water molecules.

Unless stated otherwise, the described size or size range of a particle should be considered as the mass median diameter (MMD) of the particle or set of particles. Such values are based on the distribution of the aerodynamic particle diameters defined as the diameter of a sphere with a density of 1 $gm/cm^3$ that has the same aerodynamic behavior as the particle which is being characterized. Because the particles described herein may be in a variety of densities and shapes, the size of the particles is expressed as the MMD and not the actual diameter of the particles.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention relates to dry powder formulations comprising microparticles, further comprising FDKP or $FDKP^{2-}$, and nicotine, and optionally other selected materials, wherein the microparticles fall within controlled particle size ranges. For example, in one embodiment, the formulation includes nicotine-coated FDKP microparticles, such as depicted in FIG. 6A, or nicotine-loaded FDKP and/or $FDKP^{2-}$ microparticles, such as depicted in FIG. 6B, also referred to herein as nicotine-coated microparticles, and nicotine-loaded microparticles respectively, and also collectively referred to herein as nicotine microparticles or microparticles, sized substantially between 1-10 microns, based on the MMD of the microparticles. In another embodiment, the formulation includes nicotine-coated or nicotine-loaded microparticles sized substantially between 1-7 microns. In another embodiment, the formulation includes microparticles sized substantially between 2-5 microns. In yet another embodiment, the formulation includes microparticles sized substantially between 2-3 microns. By selectively limiting or excluding nicotine microparticles below about 1 micron in size, or below about 2 microns in size, the formulations of the present invention remove or at least reduce a subject's ability to exhale nicotine back into the environment, thereby effectively reducing or removing the production of the nicotine contained in second hand smoke. Further, by selectively limiting or excluding non-respirable nicotine microparticles, the formulations of the present invention reduces unwanted irritation caused by nicotine microparticles trapped in the larger airways, oro-pharynx, the glottis vocal cords and other anatomic regions more proximal or closer to the mouth. Accordingly, in some embodiments, the smallest microparticles within the nicotine microparticles size range are at least about 1 micron, at least about 1.1 micron, at least about 1.2 micron, at least about 1.3 micron, at least about 1.4 micron, at least about 1.5 micron, at least about 1.6 micron, at least about 1.7 micron, at least about 1.8 micron, at least about 1.9 micron, or at least about 2 micron. In some embodiments, the largest microparticles within the nicotine microparticles size range are no greater than about 10 micron, no greater than about 7 micron, no greater than about 6 micron, no greater than about 5 micron, no greater than about 4.5 micron, no greater than about 4 micron, no greater than about 3.5 micron, or no greater than about 3 micron. In certain embodiments, no more than about 10% of the nicotine microparticles are less than about 1 micron. In certain embodiments, no more than about 10% of the nicotine microparticles are less than about 2 micron. In other embodiments, at least 90% of the nicotine microparticles are less than about 10 micron. In other embodiments, at least 90% of the nicotine microparticles are less than about 7 micron. In other embodiments, at least 90% of the nicotine microparticles are less than about 5 micron. In one embodiment, no more than about 10% of the nicotine particles are less than 1 micron and at least 90% of the nicotine microparticles are less than about 10 micron. In one embodiment, no more than about 10% of the nicotine microparticles are less than about 1 micron and at least 90% of the nicotine microparticles are less than about 7 micron. In one embodiment, no more than about 10% of the nicotine microparticles are less than about 2 micron and at least 90% of the nicotine microparticles are less than about 5 micron. In one embodiment, no more than about 10% of the nicotine microparticles are less than about 2 micron and at least 90% of the nicotine microparticles are less than about 3 micron.

In another example, the formulations of the present invention may optionally include a cough suppressant component having particles sized substantially between 5 and 10 microns. In one embodiment, the cough suppressant component is menthol. In another embodiment, the cough suppressant component may include benzocaine. It should be appreciated that the cough suppressant component can include any compound approved for suppressing cough. By selectively including menthol particles between 5-10 microns, these non-respirable menthol particles can reduce cough by soothing irritation in the subject's upper airways. Accordingly, in some embodiments, the smallest particles within the cough suppressant component particle size range are at least about 5 micron, at least about 6 micron, at least about 7 micron, or at least about 8 micron. In some embodiments, the largest particles within the cough suppressant component particle size range are no greater than about 10 micron, no greater than about 9 micron, no greater than about 8 micron, or no greater than about 7 micron. In certain embodiments, no more than about 10% of the cough suppressant particles are less than about 5 micron. In other embodiments, at least 90% of the cough suppressant particles are less than about 10 micron. In other embodiments, at least 90% of the cough suppressant particles are less than about 8 micron. In one embodiment, no more than about 10% of the cough suppressant particles are less than 4 micron and at least 90% of the cough suppressant particles are less than about 10 micron. In one embodiment, no more than about 10% of the cough suppressant particles are less than about 5 micron and at least 90% of the cough suppressant particles are less than about 8 micron. Although in the preferred embodiment the cough suppressant component is composed of particles substantially in the range of 5-10 micron, the cough suppressant component can comprise particles in a broader range. In one embodiment, the cough suppressant component can comprise particles in the range of 5-25 micron. In another embodiment, the cough suppressant component comprises particles substantially in the range of 5-50 micron. In yet another embodiment, the cough suppressant component comprises particles substantially in the range of 5-100 micron.

In another example, the formulation of the present invention may optionally include a cough suppressant component having particles sized substantially between 10-200 microns. This cough suppressant component can be added to the formulation instead of, or in addition to, the cough suppressant component in the range of 5-10 previously discussed. Accordingly, the formulation of the present invention can comprise two cough suppressant components, wherein each cough suppressant component has a substantially different particle size distribution. The 10-200 micron cough suppressant component may reduce a cough caused by irritation of the oro-pharynx, the glottis vocal cords and other anatomic regions more proximal or closer to the mouth that contain receptors that can trigger cough or trigger other unwanted sensations. As contemplated herein, these larger particles are substantially prohibited from entering the sub-glottic airways. Accordingly, in some embodiments, the smallest particles within the cough suppressant component particle size range are at least about 10 micron, at least about 12 micron, at least about 20 micron, at least about 30 micron, or at least about 50 micron. In some embodiments, the largest particles within the cough suppressant component particle size range are no greater than about 200 micron, no greater than about 150 micron, no greater than about 120 micron, no greater than about 100 micron, no greater than about 90 micron, or no greater than about 80 micron. In certain embodiments, no more than about 10% of the cough suppressant component particles are less than about 10 micron. In certain embodiments, no more than about 10% of the cough suppressant component particles are less than about 20 micron. In other embodiments, at least 90% of the cough suppressant component particles are less than about 200 micron. In other embodiments, at least 90% of the cough suppressant component particles are less than about 150 micron. In other embodiments, at least 90% of the cough suppressant component particles are less than about 100 micron. In one embodiment, no more than about 10% of the cough suppressant component particles are less than 10 micron and at least 90% of the cough suppressant component particles are less than about 200 micron. In one embodiment, no more than about 10% of the cough suppressant component particles are less than about 12 micron and at least 90% of the cough suppressant component particles are less than about 100 micron. In one embodiment, the cough suppressant component includes menthol particles between 10-200 microns in size, which may provide a soothing effect in areas of particle impact. In another embodiment, the cough suppressant component having particles between 10-200 microns in size may include benzocaine. It should be appreciated that the cough suppressant component having particles between 10-200 microns in size can include any compound approved for suppressing cough. In another example, the addition of at least one component in the formulation of the present invention other than the nicotine component may act to dilute the nicotine containing particles and decrease cough caused by nicotine irritating the oro-pharynx, vocal cords and other anatomic regions proximal to the trachea.

In another example, the formulation of the present invention may optionally include a flavor component having particles sized substantially between 10-1000 microns. In one embodiment, the flavor component is composed of particles substantially in the range of 10-200 micron. In a preferred embodiment, the flavor component is composed of particles substantially in the range of 10-100 micron. This flavor component utilizes such embedded larger particles that may impact the subject in the oral cavity to produce a desired flavor. Further, by limiting such flavor component particles to larger than 10 microns in size, these particles are limited in their ability to enter into the subject's lungs. Accordingly, in some embodiments, the smallest particles within the flavoring component particle size range are at least about 10 micron, at least about 12 micron, at least about 20 micron, at least about 30 micron, or at least about 50 micron. In some embodiments, the largest particles within the flavoring component particle size range are no greater than about 1000 micron, no greater than about 500 micron, no greater than about 200 micron, no greater than about 150 micron, no greater than about 120 micron, no greater than about 100 micron, no greater than about 90 micron, or no greater than about 80 micron. In certain embodiments, no more than about 10% of the flavor component particles are less than about 10 micron. In certain embodiments, no more than about 10% of the flavor component particles are less than about 20 micron. In other embodiments, at least 90% of the flavor component particles are less than about 1000 micron. In other embodiments, at least 90% of the flavor component particles are less than about 500 micron. In other embodiments, at least 90% of the flavor component particles are less than about 200 micron. In other embodiments, at least 90% of the flavor component particles are less than about 150 micron. In other embodiments, at least 90% of the flavor component particles are less than about 100 micron. In one embodiment, no more than about 10% of the flavor component particles are less than 10 micron and at least 90% of the flavor component particles are less than about 1000 micron. In one embodiment, no more than about 10% of the flavor component particles are less than 10 micron and at least 90% of the flavor component particles are less than about 200 micron. In one embodiment, no more than about 10% of the flavor component particles are less than about 10 micron and at least 90% of the flavor component particles are less than about 100 micron. In one embodiment, the flavor component is menthol. In other embodiments, the flavor component may include tobacco, fruit flavors, or food grade flavorings used in candy or baking. It should be appreciated that the flavor compound may be any flavoring compound known in the art, preferably a regulatory-approved flavoring compound.

Fumaryl Diketopiperazines

FDKP and its anionic form $FDKP^{2-}$, are chemical compounds beneficial in formulating drug compositions for delivery to the lungs, as described for example in U.S. Pat. No. 8,227,409 B2 entitled "Diketopiperazine Microparticles With Defined Isomer Contents," which is incorporated by reference herein for its teachings regarding the same. FDKP is the free acid form of fumaryl diketopiperazine as depicted in FIG. 1, and $FDKP^{2-}$ is its corresponding anion as depicted in FIG. 2. FDKP and its anion are composed of two stereoisomeric forms, trans and cis, as respectively depicted in FIG. 3. Depending on the manufacturing conditions the ratio between the two stereoisomers can be significantly varied. In one embodiment the ratio between cis and trans can be 1:1. In another embodiment disclosed herein the ratio between the two stereoisomers can be distributed in the interval from about cis to trans=3:2, to about 1:3. In other embodiments of the invention the ratio can be from about 1:1 to about 1:3.

In one embodiment FDKP is manufactured by saponification of a corresponding ester of FDKP, such as an alkyl-FDKP ester, wherein the alkyl group can be ethyl or methyl. The saponification can be carried in a solvent such as a water-based solvent by addition of a base. In a particular embodiment, the method comprises dissolving the ethyl-FDKP ester in a solvent such as water:methanol at a ratio of 1:1 to about 3:1, respectively, adding a solution comprising sodium hydroxide, holding the reaction mixture at a temperature ranging from about 200° C. to about 600° C. or to refluxing conditions, filtering the reaction mixture to yield a filtrate, adding an acidic solution to the filtrate, and collecting the solid material formed by filtration and washing the FDKP solid material. In other embodiments the invention comprises an optional recrystallization step.

The FDKP cis/trans stereoisomer ratio is established and can be controlled during the manufacturing steps described above. Parameters and/or reaction steps such as the saponification and recrystallization can be regulated to obtain a certain stereoisomer ratio. In particular temperature, reaction time, and the type of solvents or co-solvents used can be varied in order to slide back and forth the cis/trans stereoisomer ratio by epimerization, or by dynamic stereoisomer resolution during the recrystallization step.

Nicotine-Coated Microparticles

In a typical embodiment the precipitated FDKP is collected as a suspension of microparticles further used in the nicotine-coating step, such as generally described in the step-wise process depicted in FIG. 4. In some embodiments the stability of the FDKP microparticles thus obtained can be enhanced by small amounts of a surfactant, such as polysorbate-80, added to the FDKP solution from which the microparticles are precipitated. In some embodiments the solvent is removed and the microparticles are dried prior to further formulation. Appropriate methods of solvent removal include lyophilization and spray drying.

In one embodiment the FDKP microparticles thus obtained are thereafter re-suspended in an appropriate liquid, and then mixed with a nicotine solution, hereinafter referred to as the "nicotine solution," for example as depicted in FIG. 4. The microparticles/nicotine suspension thus obtained can then be pelletized (cryo-granulated) by flash freezing in liquid nitrogen, and the ice pellets can then be lyophilized to produce a dry powder. As a result of this process, the nicotine in the solution will be deposited on the surface of the FDKP microparticles in the form of an uninterrupted coating, creating unitary composite microparticles, such as for example depicted in FIG. 6A.

Nicotine-Loaded Microparticles

In another embodiment, FDKP obtained as previously described is subjected to solubilization in an appropriate solvent to afford an FDKP solution which can be further mixed with a nicotine solution, hereinafter referred to as the "nicotine solution," for example as described in the step-wise process depicted in FIG. 5. In yet another embodiment the FDKP obtained as previously described is resubjected to base treatment to afford a solution of $FDKP^{2-}$, which is further mixed with a nicotine or nicotine substitute solution, for example as described in the step-wise process depicted in FIG. 5.

In one embodiment the resulting solution comprising nicotine and FDKP and/or $FDKP^{2-}$ can be dried, such as via a spray drier, to produce nicotine-loaded composite particles such as for example depicted in FIG. 6B, that are suitable for delivery to the alveoli and lower airways of a subject. It should be appreciated that there is no limitation to the method of drying the liquid mixture. While a preferred method utilizes a spray drier, other drying techniques capable of producing appropriately sized particles may be used, such as fluidized bed drying. In one embodiment, the mixture is finely divided via passage through an orifice upon on entry to a spray dryer. In another embodiment, the mixture may be passed through an atomizer, such as a rotary atomizer, to feed the solution into a spray dryer. Further still, any rate of drying may be used (e.g., slow or rapid rate drying), provided such rate of drying results in the formation of dry particles of the desired size range. Prior to the segregation of the desired particle size of the nicotine-based component, the resultant particles formed via the spray drier may have a particle size from about 0.1 to about 5 micron.

While additional segregation/filtering of selected particle sizes may be performed subsequent to the formation of the nicotine-loaded microparticles, the operating conditions of the spray dryer may be adjusted so to produce particles which are sized so as to be able to travel to the alveoli and smaller airways of the lungs. For example, a rotary atomizer may be operated at a liquid feed rate from about 2 to about 20 ml/min, or from 2 to about 10 ml/min, or from about 2 to about 5 ml/min. Further, the rotary atomizer may be operated from about 10,000 to about 30,000 rpm, from about 15,000 to about 25,000 rpm, or from about 20,000 to about 25,000 rpm. It should be appreciated that microparticles of various sizes may be obtained by spray drying, and particles having the desired particle size may be more specifically selected when filtered, such as via one or more sieving steps, as described elsewhere herein. The spray dryer may be operated at temperatures sufficiently high to cause the liquid carrier to rapidly evolve without raising the temperature of nicotine, FDKP and/or $FDKP^{2-}$, within the mixture to a point at which these compounds begin to degrade. Accordingly, the spray dryer may be operated with an inlet temperature from about 120 to about 170° C. and an outlet temperature from about 70 to about 100° C.

It should be appreciated that the nicotine-loaded microparticles may be spherical or of any other shape desired. In one embodiment, by evolving the liquid carrier sufficiently rapidly during the spray drying process, the particles may be produced with an uneven or a "dimpled" surface. In such embodiments, the uneven surface may produce a relative turbulence as the particles travel through the air, thus providing the particles with aerodynamic lift. In such embodiments, particles having such shape may be more readily entrained, and to remain entrained, in the air inhaled by a subject, thereby improving the ability of the nicotine-based component particles to travel to the alveoli and smaller airways.

The Nicotine Solution

As contemplated herein, any form of nicotine may be used as the main component of the nicotine solution. Preferably, a form of nicotine which is soluble in or miscible with the liquid carrier of the solution is used. For example, the nicotine may be a nicotine base, which, at room temperature, is a liquid that is miscible in water. Alternatively, the nicotine base may be an oil formulation. In one embodiment, the nicotine is a salt, which, at room temperature, is a solid. The nicotine may further be a pharmacologically active analog or derivative of nicotine or substance that mimics the effect of nicotine, either alone or in combination with other active substances. If the nicotine is a base, then it may be added to the liquid carrier (such as water) and mixed to produce a generally homogeneous liquid mixture.

Accordingly, in one embodiment, nicotine is present in the formulation as a free base. In another embodiment, the formulation may comprise a nicotine salt. In one such embodiment, the nicotine salt is nicotine hydrogen tartrate. In other embodiments, the nicotine salt can be prepared from any suitably non-toxic acid, including inorganic acids, organic acids, solvates, hydrates, or clathrates thereof. Examples of such inorganic acids are hydrochloric, hydrobromic, hydroiodic, nitric, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-tolunenesulfonic, and mesylic. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like.

In one embodiment, the nicotine-based solution may include nicotine and a pharmaceutical grade sugar. As contemplated herein, the sugar is an inhalable sugar, and is generally soluble in a liquid carrier, such as water. Without limitation, examples of suitable sugars are lactose, sucrose, raffinose, trehalose, fructose, dextrose, glucose, maltose, lecitin, mannitol, or combinations thereof. In a preferred embodiment, the sugar may be alpha monohydrate lactose. The sugar may be a natural or a synthetic sugar, and may include any analogs or derivatives of sugars. It should be appreciated that any form of sugar approved as an excipient may be used as an excipient in the production of the nicotine-based solution. While not required, the sugar is preferably of a pharmaceutical grade as would be understood by those skilled in the art. It should be appreciated that there are no limitations to the ratio of nicotine to sugar used, and the actual ratio used will be based on the concentration of nicotine desired in the coating of the final product, i.e. the nicotine-coated FDKP microparticles. Accordingly, in one embodiment the ratio of sugar to nicotine in the solution may vary from about 1:100 to about 100:1, or from about 3:7 to about 3:2 or alternatively, from about 4:6 parts by weight. Further, the concentration of sugar in the solution may vary from about 1 to about 10 w/v (g/100 ml), from about 2 to about 5 w/v (g/100 ml) or from about 3% w/v (g/100 ml). In a preferred embodiment, the concentration of nicotine is between about 5-10%.

In various embodiments, the nicotine-based solution can further comprise any pharmaceutically acceptable material, composition or carrier, such as a liquid or solid filler, stabilizer, dispersing agent, suspending agent, diluent, excipient, thickening agent, solvent or encapsulating material that can promote achieving the desired properties of the nicotine coating, and ultimately confer on the invention the qualities desirable to perform its intended function. Each material must be "acceptable" in the sense of being compatible with the other ingredients of the formulation, including nicotine and FDKP or $FDKP^{2-}$, and not injurious to the subject. Some materials that may useful in the formulation of the present invention include pharmaceutically acceptable carriers, for example sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyol, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. Other pharmaceutically acceptable materials that can be useful in formulating the nicotine-based solution include any and all antibacterial and antifungal agents, and absorption delaying agents, and the like that are compatible with the activity of nicotine or any other compound useful within the invention, and are physiologically acceptable to the subject. Supplementary active compounds, including pharmaceutically acceptable salts of those compounds, may also be incorporated into the compositions. Other additional ingredients that may be included in the compositions used in the practice of the invention are known in the art and described, for example in Remington's Pharmaceutical Sciences (Genaro, Ed., Mack Publishing Co., 1985, Easton, Pa.), which is incorporated herein by reference.

Microparticles Sizing and Filtering

The formulations and methods of the present invention represent a novel product and approach to dry powder nicotine-based formulations. Unlike existing technologies which do not separate or segregate material components according to size, composition or other parameter, the present invention selectively limits particular material components of the formulation to specific and controlled particle size ranges, thereby providing a unique and superior product that delivers respirable nicotine to the alveoli and small airways while reducing or eliminating exhaled nicotine, optionally delivers a non-respirable cough suppressant to the larger airways and/or the oro-pharynx, and optionally delivers non-respirable flavor particles to the oral cavity.

As mentioned previously, the present invention includes formulations having components characterized by particular particle size ranges. For example, the formulations of the present invention can include nicotine-based particles sized substantially between 1-10 microns, and preferably between 2-5 microns. In other embodiments, the formulations can optionally include cough suppressant particles (such as menthol) having a size range of 1-100 microns. In other embodiments, the formulations can optionally include a second cough suppressant component having particles in the size range of 10-200 microns. In further embodiments, the formulations can include a flavor component (such as menthol) having particles in the size range of 10-1000 microns.

As contemplated herein, the particles of the present invention can be produced in relatively narrow size ranges via the use of at least one sieving step. In such an embodiment, the sieving step includes using a sieve corresponding to the minimum or maximum of the desired microparticle size range to eliminate microparticles from the mixture that are smaller or bigger than the desired range. For example, to obtain microparticles in the range of about 1-5 microns, a mixture of nicotine-coated or nicotine-loaded microparticles produced using the previously described processes, can first be passed through a 5 micron sieve, wherein substantially all of the microparticles smaller than 5 microns pass through the sieve and are collected. The microparticles passing through the sieve can then transferred to a 1 micron sieve, wherein substantially all of the microparticles greater than 1 micron do not pass through the sieve. The microparticles greater than 1 micron can be collected from the sieve, wherein the collected particles will be substantially sized in the range of 1-5 microns. Accordingly, such a process can be used to narrow the range of any mixture of particles to any of the desired particle size ranges as described hereinthroughout. Alternatively, the formulations are produced without a filtering step, and instead the particles are generated within the desired size range by controlling the process parameters, thus rendering the filtration steps unnecessary.

In another embodiment, a mixture of microparticles can be provided that substantially meets either the minimum or maximum criteria of the desired particle size range. For example, if a nicotine-coated or nicotine-loaded microparticle size range of 2-3 microns is desired, a mixture of microparticles can be provided wherein substantially all of the particles are less than 3 microns. Such a mixture can be produced by modifying the processes parameters such that the resulting microparticles are generally less than 3 microns. The mixture can then be transferred through a 2 micron sieve, wherein the particles not passing through the sieve are collected, and wherein the collected particles are substantially within the desired 2-3 micron range.

As would be understood by a person skilled in the art, the microparticle size ranges described herein are not absolute ranges. For example, a microparticle mixture of the present invention with a size range of 2-3 microns can contain a portion of particles that are smaller or larger than the 2-3 micron range. In one embodiment, the particle size value as presented for any particular component of the formulations of the present invention represents a D90 value, wherein 90% of the particles sizes of the mixture are less than the D90 value. In another embodiment, the particle size range represents a particles size distribution (PSD) wherein a percentage of the particles of the mixture lie within the listed range. For example, a microparticle size range of 2-3 microns can represent a mixture of microparticles having at least 50% of the particles in the range of 2-3 microns, but more preferably a higher percentage, such as, but not limited to: 60%, 70%, 80%, 90%, 95%, 97%, 98% or even 99%.

It is contemplated that the percentage of particles falling within the desired particle size range for any of the components of the formulation of the present invention can be dependent on the technique used to produce that component. For example, if the targeted size of the microparticles is in the range of 2-5 micron, it is understood that greater than 90% of that component will fall within the desired range when performing the manufacturing process on a relatively small scale. However, using a relatively large scale manufacturing process may only yield greater than 70% of the nicotine component within such a targeted range.

Excipients

As mentioned previously, the formulation may optionally include cough suppressant particles, wherein the particles of the cough suppressant component are sized between about 5 and 10 micron. By selectively including menthol particles sized between 5-10 microns, these non-respirable menthol particles can reduce cough by soothing irritation in the subject's larger airways. In another example, the formulation of the present invention may optionally include a cough suppressant component having particles sized substantially between 10-200 microns. This cough suppressant component may reduce a cough caused by irritation of the oropharynx, the glottis vocal cords and other anatomic regions more proximal or closer to the mouth that contain receptors that can trigger cough or trigger other unwanted sensations. As contemplated herein, these larger particles do not enter the sub-glottic airways because of their momentum.

In one embodiment, the cough suppressant component of either the 5-10 or 10-200 micron ranges comprises menthol. Further, it should be appreciated that any other cough suppressant compounds may be used instead of or in addition to menthol, without limitation.

As contemplated herein, any form of menthol, such as a solid form of menthol can be used for processing into menthol particles useful within the present invention. Non-limiting examples of solid forms of menthol include powders, crystals, solidified distillate, flakes, and pressed articles. In one embodiment, menthol is in the form of crystals. Menthol can be processed into particles of a size ranging from about 5 μm to about 10 μm using any method known in the art. In some embodiments, menthol is admixed with further liquid or solid additives for processing. Particulate additives can furthermore also be used. In one embodiment, menthol is admixed with silicon dioxide. In another embodiment, menthol is admixed with a sugar, such as lactose. In some embodiments, the menthol is processed in a liquid carrier.

As contemplated herein, any liquid carrier may be used in the process of producing the menthol particles. In one embodiment, the liquid carrier is water. Preferably, the liquid carrier is one in which the menthol is soluble. Accordingly, the liquid carrier may be any liquid or liquids with which menthol, either alone or in combination with an additional component, forms a flowable mixture which is preferably of a generally uniform composition.

The menthol flowable mixture may be dried, such as via a spray drier, to produce composite particles of menthol, alone or in combination with an additional component, that are suitable for delivery to the alveoli and lower airways of a person. It should be appreciated that there is no limitation to the method of drying the flowable mixture. Examples of methods for drying the flowable mixture include, but are not limited to, spray drying, vacuum drying, and freeze drying. Further still, any rate of drying may be used (e.g., slow or rapid rate drying), provided such rate of drying results in the formation of dry particles of the desired size range.

As mentioned previously, the formulation may optionally include a flavor component, wherein the particles of the flavor component are sized between about 10 and 1000 micron. In one embodiment, the flavor component comprises menthol and may be produced as previously described herein. When other flavoring compounds are used, any known processing steps suitable for such compounds may be used to produce the flavoring component within the desired particle size range of 10-1000 micron.

In various embodiments, the relative weight percentage of each component in the formulation of the present invention can be varied to achieve different characteristics. Thus, as one skilled in the art would understand, the relative weight percentages of the components can be modified for various reasons, for example, but not limited to: optimizing the cough suppressant performance of the formulation; varying or improving the taste of the formulation; and adjusting the relative dose of nicotine. In certain embodiments, the formulation can be about 1-20% by weight flavor component, with a preferred weight of 1-5% flavor component. In certain embodiments, the formulation can be about 1-10% by weight cough suppressant, with a preferred weight of 1-2.5% cough suppressant. In various embodiments, the remaining portion of the formulation, aside from any flavor components, cough suppressant components, carriers, or other components, is the nicotine component. In one embodiment, the formulation can be approximately 100% nicotine component.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A particulate formulation comprising nicotine and a diketopiperazine, wherein the diketopiperazine is fumaryl diketopiperazine(FDKP).

2. The formulation of claim 1, wherein the formulation is suitable for inhalation.

3. The formulation of claim 1, wherein the FDKP is in the anionic form of $FDKP^{2-}$.

4. The formulation of claim 1, wherein the formulation comprises nicotine-coated particles.

5. The formulation of claim 1, wherein the formulation comprises nicotine-loaded particles.

6. The formulation of claim 1, further comprising a cough suppressant.

7. The formulation of claim 1, further comprising a flavoring component.

8. The formulation of claim 1, wherein the formulation comprises particles that are substantially spherical.

9. The formulation of claim 1, wherein the formulation comprises particles that have a dimpled surface.

* * * * *